United States Patent [19]

Javitt

[11] Patent Number: 6,162,827
[45] Date of Patent: *Dec. 19, 2000

[54] TREATMENT OF NEGATIVE AND COGNITIVE SYMPTOMS OF SCHIZOPHRENIA WITH D-SERINE

[75] Inventor: Daniel C. Javitt, Riverdale, N.Y.

[73] Assignee: Daniel Javitt, Riverdale, N.Y.

[*] Notice: This patent is subject to a terminal disclaimer.

[21] Appl. No.: 09/212,273

[22] Filed: Dec. 16, 1998

Related U.S. Application Data

[62] Division of application No. 08/759,714, Dec. 6, 1996, Pat. No. 5,854,286.
[60] Provisional application No. 60/008,361, Dec. 7, 1995.

[51] Int. Cl.$^7$ .................................................. A61K 31/20

[52] U.S. Cl. .............................................................. 514/561

[58] Field of Search ............................................. 514/561

[56] References Cited

U.S. PATENT DOCUMENTS

| | | |
|---|---|---|
| 4,904,681 | 2/1990 | Cordi et al. . |
| 5,068,412 | 11/1991 | Ohfune et al. . |
| 5,086,072 | 2/1992 | Trullas et al. . |
| 5,179,085 | 1/1993 | Bigge et al. . |
| 5,187,171 | 2/1993 | Cordi et al. . |
| 5,260,324 | 11/1993 | Cordi et al. . |
| 5,428,069 | 6/1995 | Skolnick et al. . |
| 5,656,608 | 8/1997 | Schneider et al. ........................ 514/42 |
| 5,837,730 | 11/1998 | Javitt et al. .............................. 514/551 |
| 5,854,286 | 12/1998 | Javitt et al. .............................. 514/561 |

OTHER PUBLICATIONS

Andreasen N (1989): The scale for the assessment of negative symptoms (SANS): conceptual and theoretical foundations. Br J Psychiatry 155 (suppl. 7):49–52.

Costa J, Khaled E, Sramek J, Bunney W Jr, Potkin SG (1990): An open trial of glycine as an adjunct to neuroleptics in chronic treatment–refractory schizophrenics J Clin Psychopharmacol 10:71–72.

D'Souza DC, Morrissey K, Abi–Saab D, Damon D, Gil R, Bennett A, Krystal JH (1995): Intravenous glycine and oral D–cycloserine effects on CSF amino acids, plasma hormones, and behavior in healthy humans: Implications for schizophrenia. Schiz Res 15:147, 1995.

Javitt DC and Zukin SR (1991): Recent advances in the phencyclidine model of schizophrenia. Am J Psychiatry 148: 1301–1308.

Javitt DC, Zylberman I, Zukin SR, Heresco–Levy U, Lindenmayer JP (1994): Amelioration of negative symptoms in schizophrenia by glycine. Am J Psychiatry 151:1234–1236.

Johnson JW. Ascher P. Glycine potentiates the NMDA response in cultured mouse brain neurons. Nature. 325:529–31, 1987.

Kay SR, Fiszbein, Opler LA (1987): The positive and negative syndrome scale (PANSS) for schizophrenia. Schiz Bull 13:261–276.

Leiderman Eduardo, Zylberman Ilana, Zukin Stephen R, Cooper Thoms B, Javitt Daniel C. (1996): Preliminary Investigation of High–Dose Oral Glycine on Serum Levels and Negative Symptoms in Schizophrenia: An Open–Label Trial. Biol Psychiatry 39:213–215.

Potkin SG, Costa Roy S, Sramek J, Jin Y, Gulasekaram B (1992): Glycine in the treatment of schizophrenia—theory and preliminary results, in Novel Antipsychotic Drugs. Edited by Meltzer HY. New York, Raven Press.

Rosse RB, Theut SK, Banay–Schwartz M, Leighton M, Scarcella E, Cohen CG, Deutsch SI (1989): Glycine adjuvant therapy to conventional neuroleptic treatment in schizophrenia: an open–label, pilot study. Clin Neuropharmacol 12:416–24.

Waziri R (1989): Glycine therapy of schizophrenia. Biol Psychiatry 1988, 23:210–211 (letter).

M. Nilsson, et al., "Glycine and D–serine decrease MK–801–induced hyperactivity inmice" Journal of Neural Transmission (1997) 104: 1195–1205.

John P. Kaltenbach, et al., "Compounds Protective againsht Renal Tubular necrosis Induced by D–Serine and D–2, 3–Diaminoproplonic Acid in the Rat$^1$"Experimental and Molecular Pathology 27,225–234 (1982).

Frank A. Carone, et al., "Urinary Loss of Glucose, Phosphate, and Protein by Diffusion into Proximal Straight Tubules Injured by D–Serine and Maleic Acid" Laboratory Investigation, vol. 52, No. 6, pg. 605, 1985.

Katsunobu Takahashi, et al., "In Vivo Evidence for the Link Between L–and D–Serine Metabolism in Rat Cerebral Cortex." Journal of Neurochemistry, vol., 69, No. 3, 1997.

Taka–aki Matsui, et al., "Functional Comparison of D–Serine and Glycine in Rodents: The Effect on Cloned NMDA Receptors and the Extracellular Concentration" Journal of Neurochemistry Vo. 65, No. 1, 1995.

Guochuan Tsai, et al., "D–Serine Added to Antipsychotics for the Treatment of Schizophrenia" Society of Biological Psychiatry 1998, vol. 44 pg. 1081–1089.

Toth Eugene, Weiss Benjamine, Banay–Schwartz Miriam, Lajtha Abel (1986): Effect of Glycine Derivatives on Behavioral Changes induced by 3–Mercaptopropionic Acid or Phencyclidine in Mice 11:1–8.

Ishimaru M, Kurumaji A, Toru M (1994) Increases in strychnine–insensitive glycine binding sites in cerebral cortex . . . evidence for the glutamate hypothesis, Biol. Psychiatry 35:84–95.

(List continued on next page.)

Primary Examiner—Keith D. MacMillan
Attorney, Agent, or Firm—Sughrue, Mion, Zinn, Macpeak & Seas, PLLC

[57] ABSTRACT

The amino acid glycine in an administered amount of above 0.4 g/Kg/day is used for treating symptoms of psychosis and of schizophrenia.

1 Claim, 7 Drawing Sheets

OTHER PUBLICATIONS

Kretschmer BD, Schmidt WJ (1992), Glycine agonists in the treatmen tof schizophrenia? Clin Neuropharmacol, 15:157–159.

Olney JW, Farber NB (1995) Glutamate receptor dysfunction and schizophrenia, Arch. Gen. Psychiatry, 52:998–1007.

Rosse Rb, Schwartz BL, Davis RE, Deutsch SI (1991), An NMDA intervention strategy in schizophrenia with "low dose" milacemide, Clin Neuropharmacol, 14:268–272.

Rosse RB, Fay=McCarthy M, Kendrick K, Davis RE, Deutsch SI (1996), D–cycloserine adjuvant therapy to molindone in the treatment of schizophrenia, Clin Neuropharmaol, 19:444–50.

Waziri R (1996), Glycine therapy of schizophrenia: some caveats, Biol Psyciatry, 39:115–6.

Wood PL (1995): The co–agonist concept: is the NMDA–associated glycine receptor saturated in vivo? Life Sci 57:301–10.

Toth et al. (1982): Elevation of Cerebral Levels of Nonessential Amino Acids in vivo by Administration of Large Doses, Neurochemical Research, 6, (12).

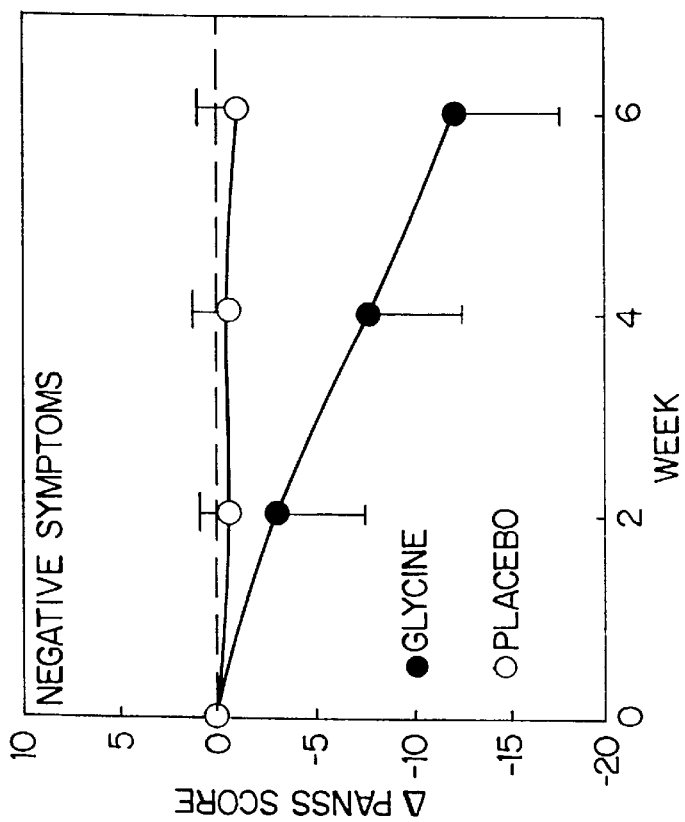
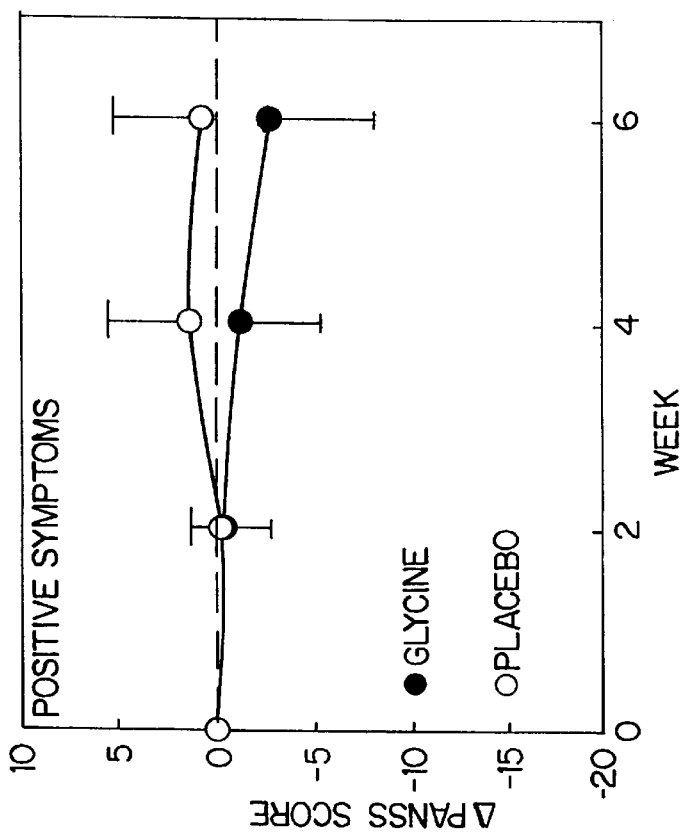
FIG. 2(a)
FIG. 2(b)

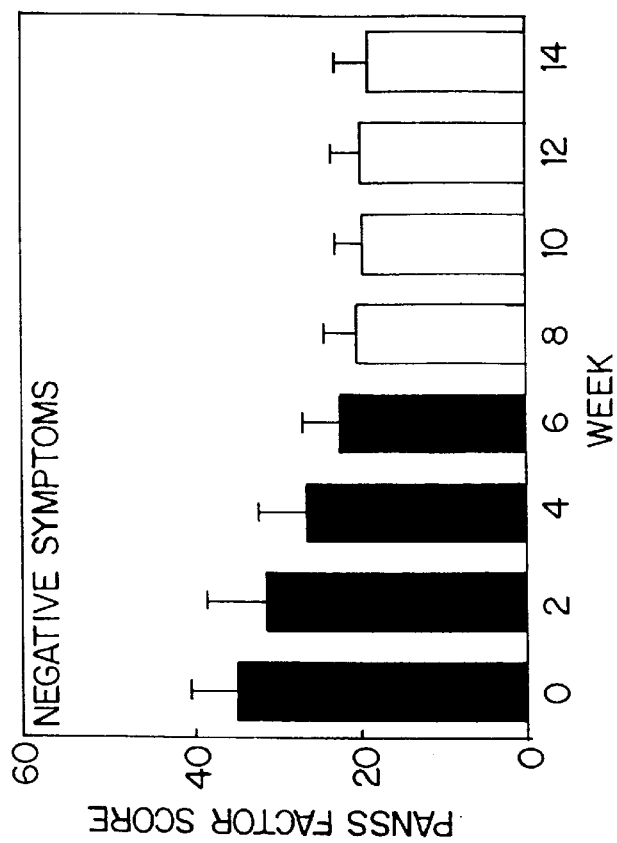
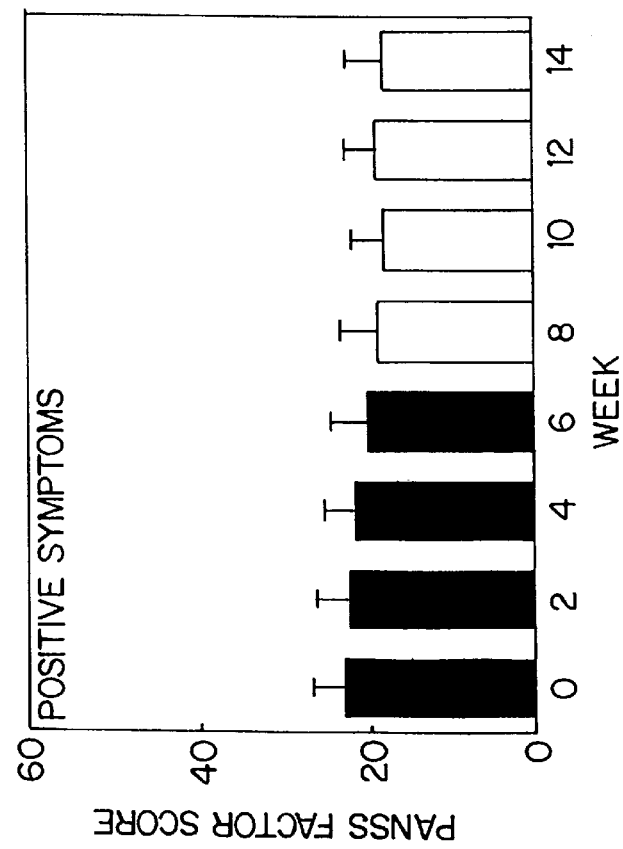

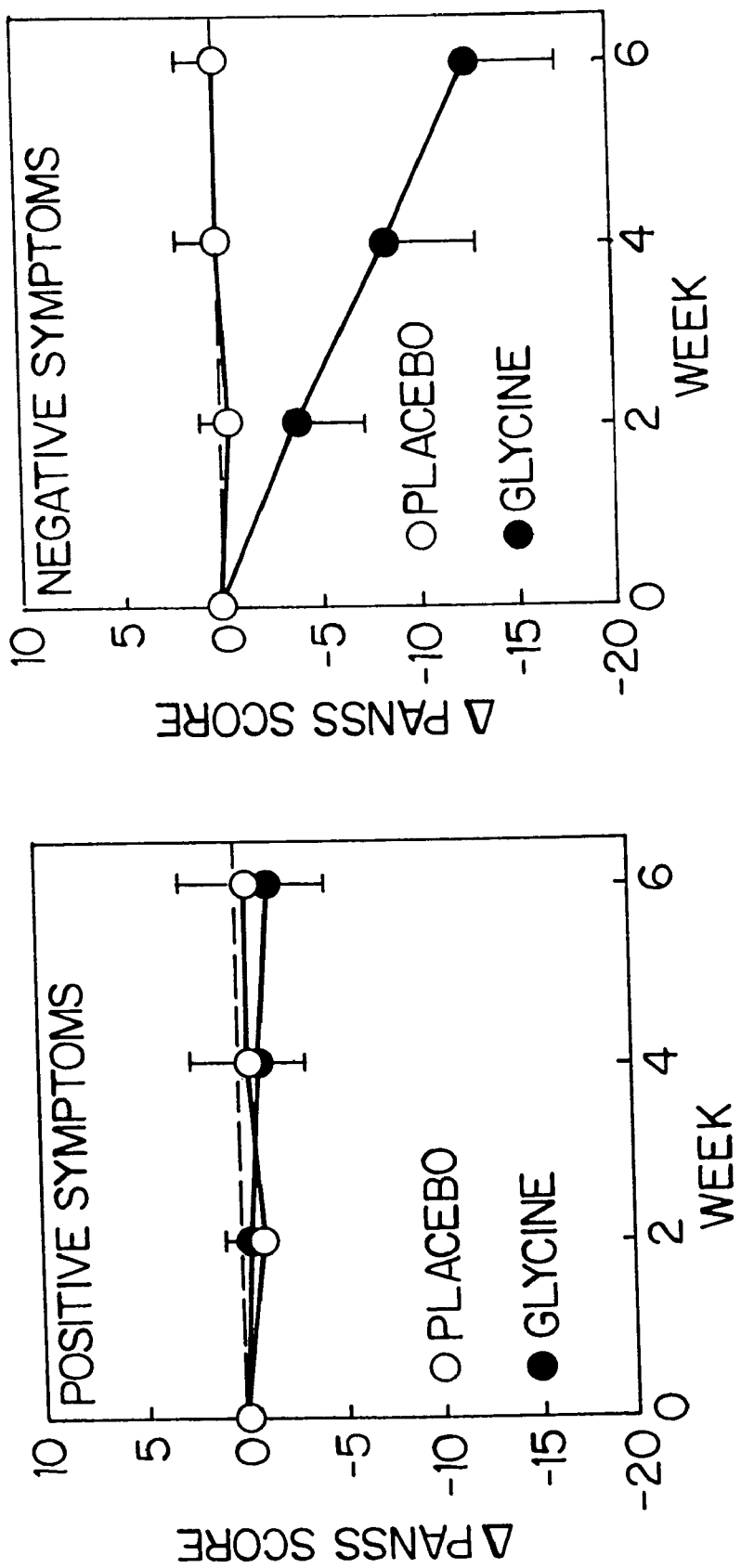

TREATMENT OF NEGATIVE AND COGNITIVE SYMPTOMS OF SCHIZOPHRENIA WITH D-SERINE

RELATED APPLICATION

This application claims benefit of provisional application 60/008,361 filed Dec. 7, 1995.

This is a divisional application of application Ser. No. 08/759,714, filed Dec. 6, 1996, the disclosure of which is incorporated herein by reference, and which is now U.S. Pat. No. 5,854,286.

BACKGROUND OF THE INVENTION

For the past 30 years, the dopamine hypothesis has been the leading neurochemical model of schizophrenia. The dopamine hypothesis is based upon observations that amphetamine-like dopamine releasing agents induce a psychotomimetic state that closely resembles schizophrenia and that agents that block dopamine receptors (e.g., chlorpromazine, haloperidol) are clinically beneficial in the treatment of schizophrenia. The dopamine hypothesis posits that symptoms of schizophrenia reflect functional hyperactivity of brain dopaminergic symptoms, primarily in the mesolimbic and mesocortical brain regions. Despite its heuristic value, however, there are several limitations of the dopamine hypothesis that have contributed to limitations in clinical treatment in schizophrenia. First, amphetamine psychosis provides an accurate model only for the positive symptoms of schizophrenia (e.g., hyperactivity, hallucinations). In contrast, amphetamine administration does not lead to the development of negative symptoms (e.g., blunted affect, emotional withdrawal) or cognitive dysfunction similar to that observed in schizophrenia. A significant percentage (20–50%) of schizophrenic patients continue to show prominent negative symptoms and thought disorder despite optimal treatment with dopamine-blocking agents, indicating that new treatment approaches are necessary. Second, for the majority of schizophrenic patients no clear disturbances of dopaminergic neurotransmission have been demonstrated. Thus, to the extent that functional dopaminergic hyperactivity does exist, it may be secondary to a more fundamental disturbance in other neurotransmitter systems. Antidopaminergic treatment, therefore, while controlling symptoms may not address underlying pathophysiology.

A potential direction for the development of a new treatment approach first became available in the late 1950's with the development of phencyclidine (PCP, "angel dust"). PCP was initially developed for use as a general anesthetic. In early clinical trials, PCP and related agents (e.g., ketamine) were found to induce psychotic symptoms that closely resembled those of schizophrenia. As opposed to amphetamine psychosis, PCP psychosis incorporated both negative and positive symptoms of schizophrenia. Moreover, PCP uniquely reproduced the type of cognitive dysfunction seen in schizophrenia. Mechanisms underlying PCP-induced psychosis remained largely unknown until the initial description of brain PCP receptors in 1979. Subsequent research in the early 1980s demonstrated that the PCP receptor constitutes a binding site located within the ion channel associated with N-methyl-D-aspartate (NMDA)-type glutamate receptors, and that PCP and related agents induce their psychotogenic effects by blocking NMDA receptor-mediated neurotransmission. This finding led to the suggestion (Reference 15; Reference 5) that endogenous dysfunction or dysregulation of NMDA receptor-mediated neurotransmission might contribute significantly to the etiology of schizophrenia, and, in particular, might lead to the expression of neuroleptic-resistant negative and cognitive symptoms. Further, it raised the possibility that medications that could potentiate NMDA receptor-mediated neurotransmission might be beneficial in the treatment of neuroleptic-resistant signs and symptoms of schizophrenia.

Prior to discovery of the glycine binding site in 1987, it was found that administration of oral glycine to rodents at high doses similar to those used later by the present inventor leads to reversal of behavioral effects induced by PCP Reference 14), indicating that that behavioral essay may be sensitive to the anti-psychotic effects of NMDA augmenting agents.

NMDA receptors are primarily activated by glutamate, which serves as the major excitatory neurotransmitter in cortex. Exogenous glutamate cannot be administered effectively, however, because (1) glutamate does not cross the blood-brain barrier, (2) glutamate activates several types of receptors other than NMDA receptors, and (3) activation by glutamate analogs that cross the blood-brain barrier may lead to overexcitation of cortical neurons, resulting in neuronal degeneration (excitotoxicity). A potential alternate approach for potentiating NMDA receptor-mediated neurotransmission became available in 1987 with the demonstration that glycine acts as an allosteric modulator at the NMDA receptor complex (Reference 7). This finding raised the possibility that exogenously administered glycine might selectively potentiate NMDA receptor-mediated potentiation and might, therefore, lead to clinical improvement in schizophrenic patients with prominent neuroleptic-resistant symptomatology. Limitations to the use of glycine were (1) it was unknown to what extent exogenously administered glycine might permeate the CNS, (2) it was unknown to what extent glycine regulation of NMDA receptor-mediated neurotransmission would be of physiological relevance in vivo, and (3) it was unknown to what extent augmentation of NMDA receptor-mediated neurotransmission might, in fact, lead to clinical improvement.

Subsequent to the discovery of the glycine binding site in 1987, several small clinical trials were attempted which were suggestive of possible beneficial clinical effects but which failed to demonstrate efficacy using standard statistical approaches. Waziri in 1988 (Reference 12) published regarding the treating of 11 schizophrenic patients with doses of 5–25 g/day in an open study which lasted 9 months. They reported improvement in 4 of the 11 patients, but failed to provide a control group or statistical analysis of their results. Costa et al., in 1990 (Reference 2) published their work on treating 6 patients with doses of 15 g/day of glycine in a 5 week open design, and observed positive responses in 2 patients, as reflected in a greater than 30% decrease in symptoms as measured by the Brief Psychiatric Rating Scale (BPRS). However, overall statistical analysis was not performed, and independent analysis of their published data does not reveal a statistically significant effect (t=1.89, p=0.12). A subsequent study (Reference 13) of 18 patients in a double-blind study of 15 g/day of glycine vs. placebo showed significant improvement in Clinical Global Impression (CGI), but did not show significant improvement in either the BPRS or a scale developed specifically for the assessment of negative symptoms, the Schedule for Negative Symptoms (SANS). Although it was concluded by these authors that use of higher doses of glycine might be required to demonstrate efficacy, no follow-up studies were conducted. Rosse et al., (Reference 11, 1989) administered 10.8 g/day glycine to 6 chronic schizophrenic subjects for periods of 4 days to 8 weeks in an open-design but failed to observe overall clinical efficacy. These authors also concluded that this treatment approach was limited by the poor CNS permeation of glycine. Until 1994, no clinical studies were performed by any group with doses greater than 25 g/day, and the practicality of using glycine at higher doses was not determined.

The first study to be performed with higher doses of glycine was initiated by the applicant in 8/89. In this study, 14 chronic schizophrenic subjects with neuroleptic-resistant symptomatology were treated with 0.4 g/Kg/day (approx. 30 g/day) in a double-blind placebo-controlled fashion and positive and negative symptoms were monitored using the Positive and Negative Symptom Scale (PANSS). This study validated the use of high doses of glycine in that the medication was well tolerated. Moreover, preliminary encouraging results were obtained such that significant improvement in negative symptoms was observed in the glycine-treated subjects, whereas no similar improvement was observed in those treated with placebo. However, the study remained inconclusive in that no significant difference was observed between the glycine- and placebo groups. Results of this study were published in August, 1994 (Javitt et al., 1994, Reference 6).

SUMMARY OF THE INVENTION

The present invention involves treatment with ultra-high (>30 g/day) doses of glycine for effective augmentation of NMDA receptor-mediated neurotransmission and for treatment of illness associated with psychosis and psychosis associated with drug intoxication, especially schizophrenia in vivo. Two recently completed studies now validate this concept. In the first study (Leiderman et al., Reference 9), 5 schizophrenic subjects who had participated in the applicant's original 30 g/day glycine study at Bronx Psychiatric Center were rechallenged with a dose of 60 g/day. Glycine levels were monitored along with positive and negative symptoms, which were rated using both the SANS and PANSS. Treatment with 60 g/day of glycine was found to lead to a 6.3-fold increase in serum glycine levels Such a rise in serum levels has been shown by others (D'Souza et al., 1995, Reference 3), to lead to an approximate doubling of CNS glycine levels. Thus, doses in excess of those used in prior studies (i.e., in excess of 30 g/day) may be required to significantly affect CNS glycine levels. No significant side effects were observed during treatment with 60 g/day of glycine. Thus, this study provides the first evidence of the practicality of clinical treatment with high-dose glycine. Finally, despite the small number of subjects significant improvement was observed on SANS negative symptoms (<0.05) and a trend toward significant improvement was observed on the PANSS, indicating potential efficacy of ultra-high dose glycine.

A second recently completed study provides more definitive evidence for the effectiveness of 60 g/day in the treatment of neuroleptic-resistant negative symptoms. This study was conducted by a former Bronx Psychiatric Center Schizophrenia Research Fellow, Dr. Uri Heresco-Levy, at the Sarah Herzog Hospital in Israel, using the protocol developed by the applicant. Subjects were treated with 60 g/day of glycine vs. placebo in a double-blind crossover design. Results from the first 11 subjects were transmitted for analysis. These results demonstrate significantly greater reduction in PANSS negative symptoms in schizophrenic patients during the glycine-treatment phase than during the placebo-treatment phase. Thus, this study provides the first double blind, placebo-controlled evidence for efficacy of high-dose glycine treatment. Significant improvement was also observed in other aspects of schizophrenic symptomatology including general psychopathology and cognitive functioning. No significant side-effects were observed in any of the treated subjects.

Although the concept that treatment with oral glycine might be of significant clinical benefit in schizophrenia has been discussed in prior papers, the above-noted two recently completed studies (BPC and Israel) provide the first definitive evidence of the invention disclosed herein, that a high dose treatment is safe, practical and efficacious.

Up to 50% of schizophrenic subjects continue to show prominent negative and cognitive symptoms following treatment with neuroleptic medications. Newly developed agents, such as clozapine and risperidone, may show some improved efficacy compared to standard neuroleptics. Despite the introduction of such medications, however, significant numbers of schizophrenic patients remain chronically hospitalized. Treatment of such patients with glycine at doses of 30 g/day or above will lead to significant clinical improvement, and would thus address a clinical need that is not presently targeted by other available medications.

It has now been found treatment of psychotic conditions such as schizophrenic subjects with high (>30 g/day)-doses of oral glycine leads to significant improvement in negative symptoms, depression and cognitive dysfunction without affecting positive symptoms or excitement. The dose (0.8 g/Kg/day or approx. 60 g/day) that was used for the studies cited in this application are substantially higher than the doses used in any prior study. Moreover, the serum glycine levels that resulted from the administration of 0.8 g/Kg/day of glycine are within the range of levels that are known to be associated with significant elevations of CNS glycine levels. The dosage range for the administration of glycine in accordance with this invention is above 0.4 g/Kg/day to about 2.0 g/Kg/day.

In another embodiment of this invention, agents are administered which induce elevations in overall CNS glycine levels by serving as glycine precursors or which would substitute for glycine at the glycine site of the NMDA receptor complex. Such agents would include, but not be limited to, glycinamide, threonine and D-serine.

In the above embodiment (use of precursors), the precursor is administered in an amount sufficient for providing an equivalent elevation of extracellular glycine in the brain.

In still another embodiment of the invention, psychosis associated with other psychiatric conditions including drug-induced (phencyclidine, ketamine and other dissociative anesthetics, amphetamine and other psychostimulants and cocaine) psychosis, psychosis associated with affective disorders, brief reactive psychosis, schizoaffective psychosis, and psychosis NOS, "schizophrenia-spectrum" disorders such as schizoid or schizotypal personality disorders, or illness associated with psychosis (such as major depression, manic depressive (bipolar) disorder, Alzheimers disease and post-traumatic stress syndrome) is treated.

In another embodiment of this application glycine or glycine precursors would be administered parenterally.

Other objects of the invention will be apparent to the skilled artisan from the detailed description of the invention herein.

DETAILED DESCRIPTION OF THE INVENTION

Figure 1:
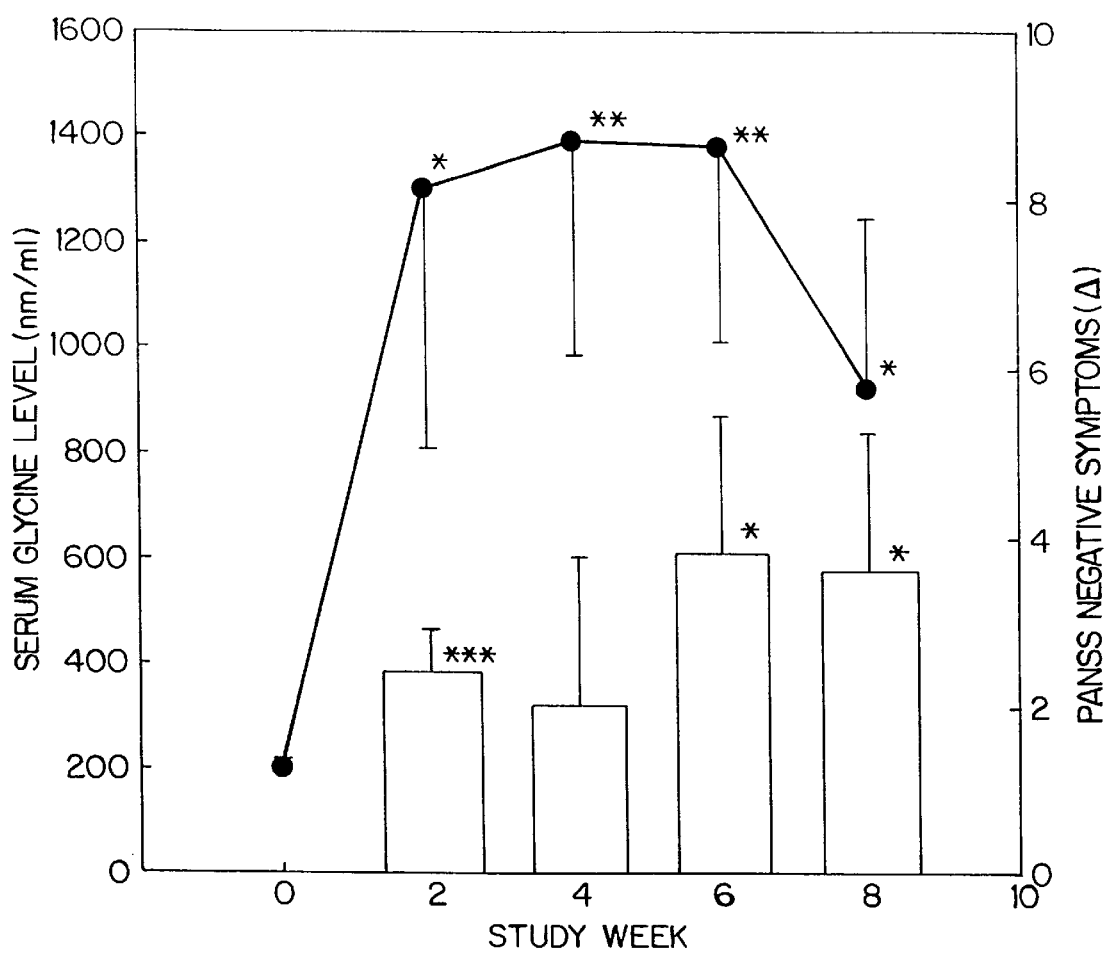
FIG. 1 of the drawing depicts effect of 0.8 g/Kg/day of oral glycine on serum glycine levels (scatter plot) and negative symptoms (bar plot) as determined using the Positive and Negative Symptom Scale (PANSS) (Kay et al., 1987, Reference 8) which includes such items as blunted affect, emotional or withdrawal, and difficulty in abstract thinking from Study #1. All statistics were performed using paired, two tailed t-tests (* $p<0.1$ vs. baseline (week 0),  $p<0.05$ vs. baseline, * $p<0.01$ vs. baseline).

Administration can be through the use of liquid and solid formulations and also through the use of injectables, such as intravenous injectables, wherein conventional pharmaceutical carriers would be employed. Suitable pharmaceutical preparations include tablets, capsules, oral liquids and parenteral injectables. Tablet and capsule formulations can be employed utilizing conventional diluents, excipients, and the like such as lactose in conventional capsule and tablet-making procedures. When administered as an oral liquid, the compound glycine has a sweetish flavor that can be made more palatable through the use of pleasant tasting diluents.

The compound for the present invention is to be administered at a dose of above 0.4 g/Kg/day, for example, 0.5 g/Kg/day or above in one to several doses, preferably in a dose of 0.8 g/Kg/day divided into three equal doses. Up to 140 grams per day glycine (about 2.0 g/Kg/day) can be administered, e.g., doses of 35, 40 or 60 grams per day. The glycine is given as the sole treatment for the psychotic-related condition, or is used adjunctively to conventional antipsychotic drugs such as haloperidol (Haldol®), fluphenazine (Prolixin®), chlorpromazine (Thorazine®) or thioridazine (Mellaril®), to atypical antipsychotic drugs such as clozapine (Clozaril®) and risperidone (Risperdal®), to medications used for the control of antipsychotic medication side effects, and to other medications commonly used for control of symptoms in conditions and illnesses such as schizophrenia.

When given in doses as herein, glycine exerts a clinically beneficial effect on symptoms of schizophrenia, in particular on negative symptoms and cognitive dysfunction. The beneficial effects of glycine on negative symptoms occur in the absence of deterioration in any other aspects of schizophrenia, such as positive symptoms or excitement. In one embodiment of the invention, glycine administration would be continued indefinitely for control of symptoms that do not respond adequately to traditional classes of medication.

The following examples are provided to illustrate the effectiveness of glycine for the treatment of schizophrenia.

Study #1 (Leiderman et al., supra.)

Methods: This study was conducted at the Bronx Psychiatric Center in the Bronx, N.Y. Five DSM-IV schizophrenic patients chosen because of participation in a prior double-blind study with 0.4 g/Kg/day of glycine entered this study after providing informed consent. Their mean age was 45.0±7.6 years old and their mean chronicity of illness 24.2±5.9 years. All were considered markedly to severely ill (CGI >4). All patients were receiving antipsychotics (2 clozapine, 2 risperidone and 1 haloperidol), on which they had been maintained for at least 4 weeks prior to the trial.

Oral glycine was added to their neuroleptic regimen at a dose of 10 g/day (~0.14 g/Kg/day), and incremented to 0.2 g/Kg/day (~14 g/day) at day 3. Glycine dose was increased by 0.2 g/Kg/day every 2 days until a dose of 0.8 g/Kg/day was reached, and was then maintained for the remainder of the 8 weeks treatment period. Biweekly ratings were performed using the Positive and Negative Syndrome Scale (PANSS) (Kay et al., 1987, Reference 8) and the Scale for the Assessment of Negative Symptoms (SANS) (Andreasen, 1989, Reference 1).

The Extrapyramidal Rating Scale (ERS) and the Abnormal Involuntary Movement Scale (AIMS) were used to measure motoric side effects. All ratings were performed by a single individual who was blind to outcome of the prior glycine treatment study. Glycine and neuroleptic blood levels for haloperidol and clozapine were obtained every two weeks. Plasma glycine was determined by a liquid chromatographic procedure (Harihan et al., 1993, Reference 4) for plasma amino acids and optimized for glycine using O-methylserine as an internal standard.

Values in text represent mean±standard deviation. Treatment effects were determined using two-tailed, paired t-tests.

Results: Treatment with oral glycine led to a significant, 6.3-fold increase in glycine blood levels that remained stable from week 2 to week 6 (FIG. 1). There was an apparent decrease in glycine level between weeks 6 and 8, although the difference did not reach statistical significance. No adverse effects, including weakness, nausea or sedation were seen in any patient during the 8 weeks of the trial.

A significant improvement in negative symptoms was found using the SANS (baseline: 75.8±7.2 vs. end of study: 72.2±8.6, t=2.79, p=0.049) and a trend towards improvement, using the PANSS negative symptom scale (baseline: 31.0±2.3 vs. end of the study: 27.4±3.2, t=2.21, p=0.092). Two of the 5 subjects experienced a greater than 20% reduction in negative symptoms. Treatment response was not significantly correlated with glycine level either across subjects or across time within individual subjects.

Of the patients included in this study, those who showed the greatest treatment response to glycine were those who had shown the greatest response to prior double-blind treatment with 0.4 g/Kg/day of glycine (Javitt et al., 1994, supra.). There was thus a significant across-subject correlation between change in total PANSS score observed in the present study and that observed in the prior study (r=0.82, p=0.045). As in the prior study, there were no significant changes in PANSS positive symptoms (t=1.68, df=4, p=0.17) or general psychopathology (t=0.72, df=4, p=0.5) in the present study. There was a significant reduction in extrapyramidal (t=4.81, df=4, p=0.009), but not dyskinetic (t=0.91, df=4, p=0.4), symptoms during glycine treatment. However, there was no correlation between improvement in extrapyramidal symptoms and clinical response. Glycine treatment did not significantly affect serum neuroleptic levels.

Study #2—Heresco-Levy, et al., above

Methods: Subjects consisted of inpatients drawn from the research unit of the Sarah Herzog Memorial Hospital, Jerusalem, Israel. Subjects were diagnosed with schizophrenia according to DSM-III-R (American Psychiatric Association, 1987). Subjects, moreover, were considered to be treatment resistant on the basis of poor response to prior neuroleptics. Prior to study entry, subjects had been treated with stable, clinically determined optimal oral doses of conventional neuroleptics or clozapine for at least 3 months. Schizophrenic patients who met the criteria of additional DSM-III-R diagnoses, were receiving additional psychotropic medications or had a concurrent medical or neurological illness were excluded. Twelve patients were enrolled in the study. All subjects gave written informed consent to participate and the study was approved by the institutional review board.

After a 2 week (week −2 to week 0) baseline assessment period, subjects were randomly assigned to receive, under double-blind conditions, either glycine powder or placebo solution for six weeks (week 0–week 6). Medication was administered under double blind conditions. Glycine powder was administered dissolved in water. The placebo solution consisted of glucose. Each patient then underwent a 2 week adjunctive treatment washout period after which he/she crossed over to the alternate substance for another 6 weeks (week 8–week 14). Glycine administration was initiated at a dose of 4 g/day and was increased by 4 g/day until a fixed daily dose equivalent to 0.8 g/Kg body weight was reached. Daily glycine treatment was administered in three divided doses. The only other medications allowed during the study were trihexyphenidyl (2–5 mg/day) for treatment of extrapyramidal symptoms and chloral hydrate (250–750 mg/day on PRN basis) for treatment of insomnia or agitation. For patients needing antiparkinsonian medication, trihexyphenidyl dose was kept constant throughout the study.

Symptoms and extrapyramidal side effects were assessed starting from week −2, biweekly throughout the study, using the PANSS, the Simpson-Angus Scale for Extrapyramidal Symptoms (SAS) and the Abnormal Involuntary Movement Scale (AIMS). Patients requiring, at any point during the study, neuroleptic dose increases were withdrawn from the study and appropriate treatment was instituted. Withdrawal decisions were based on clinical evaluations and coincided with an increase of at least 30% on the PANSS score.

Physical complaints and status were monitored daily. Hematology, blood chemistry, liver and kidney function, laboratory measures were assessed biweekly. Blood samples for the assessment of glycine serum levels were obtained at baseline and at the end of study weeks 6 and 14. Blood drawings were performed before breakfast and first daily administration of medication. Serum glycine levels were determined on a Perkin Elmer-Pickering Amino Acid Analyzer using a lithium pH gradient and postcolumn derivation with ninhydrin. Quantification was carried out using a UV detector at 570 mn. Calculations were based on a nor-leucine internal standard. Statistical analyses (two-tailed) were performed using the SPSS/PC computer program.

Results: Of the 12 patients who entered the study, 11 completed. The one early termination occurred at week 4 of placebo treatment. Of the patients who completed, 7 had been randomized to receive glycine during the first phase of the study, while the remaining 4 had been randomized to receive placebo. All patients showed stable pretreatment baselines as evidenced by a lack of change in positive and negative symptoms during the two weeks prior to double-blind treatment (Table 1). Pretreatment baselines did not differ among those subjects who received glycine during the first double-blind treatment phase and those who received placebo.

In order to assess treatment response to glycine relative to placebo, rmANOVA were performed across all subjects with within-subject factors of treatment phase (glycine/placebo) and treatment week (0, 2, 4 or 6). Highly significant between-treatment differences were observed for negative symptoms and general psychopathology, as reflected in significant treatment by time interactive effects, with no corresponding worsening of positive symptoms (Table 2). However, when changes in general psychopathology and total PANSS score were covaried for changes in negative symptom score, no significant treatment or treatment by time effects were observed, indicating that the changes in general psychopathology might have been secondary to changes in negative symptoms. Significant effects of glycine on total PANSS score was also observed. As with the general psychopathology effects, changes in total PANSS score were not significant following covariation for changes in negative symptoms. In order to assess the possibility that treatment order affected overall results, rmANOVA of negative symptoms by treatment phase and week were covaried for treatment order. Significance of the treatment by time effect $F(3,8)=42.6$, $p<0.0001$), indicating that results were not significantly affected by treatment order.

Figure 2D:
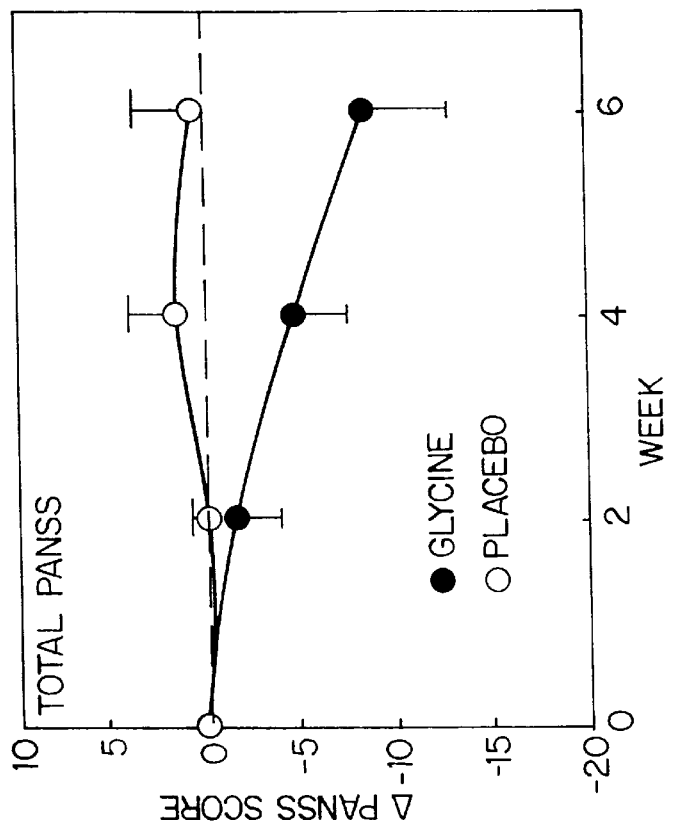
FIG. 2 (a)–(d) of the drawing depicts, from Study #2, three-factor and total PANSS change scores during double-blind adjunctive treatment with glycine and placebo (* $p<0.05$,  $p<0.01$, * $p<0.001$).
Figure 2C:
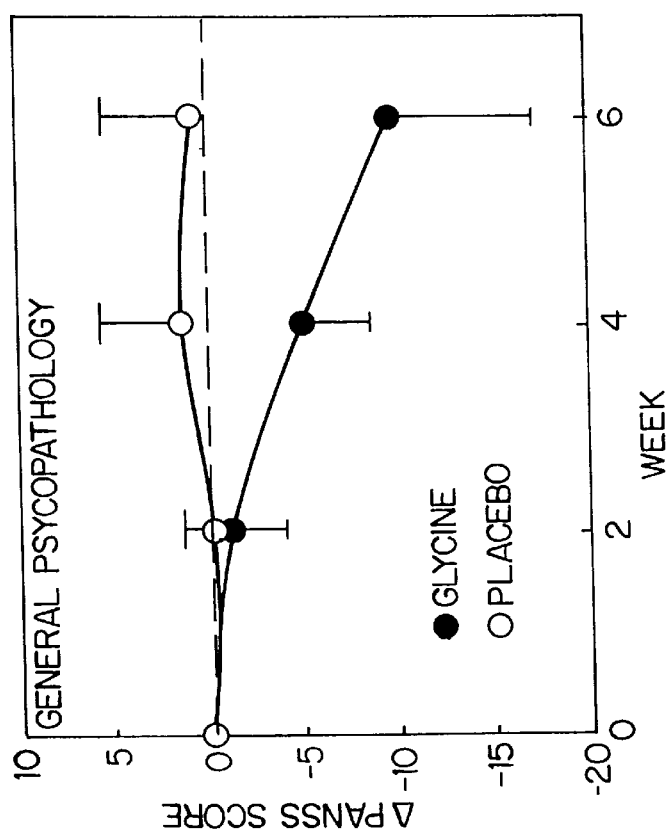

Analysis of symptom change scores revealed that significant reductions in negative symptoms were apparent by week 2 of the glycine treatment phase and increased progressively until termination of glycine treatment after week 6 (FIG. 2). The mean percentage reduction in negative symptoms at 6 weeks was $36.2 \pm 7.3\%$ compared to preglycine treatment values $t=0.22$, $df=10$, $p<0.0001$). Reductions in general psychopathology were first apparent after 4 weeks of glycine treatment and increased progressively thereafter. Mean reduction in general psychopathology was $23.5 \pm 10.5\%$ ($t=7.41$, $df=10$, $p<0.0001$). A small reduction in positive symptoms was also observed in the glycine treatment group ($12.6 \pm 18.3\%$). Although this effect was significant when compared to preglycine treatment values ($t=2.29$, $df=10$, $p<0.05$), changes in positive symptoms at the end of 6 weeks of glycine treatment were not significantly greater than changes following 6 weeks of placebo (FIG. 2). 8 of the 11 subjects had PANSS negative symptoms decreases of 30% or more and PANSS total score decreases of 25% or more during treatment with glycine. No reductions in symptoms of any type were apparent during the placebo treatment phase, and a small but significant increase in general psychopathology was observed at week 4 of the placebo treatment period.

Figure 3D:
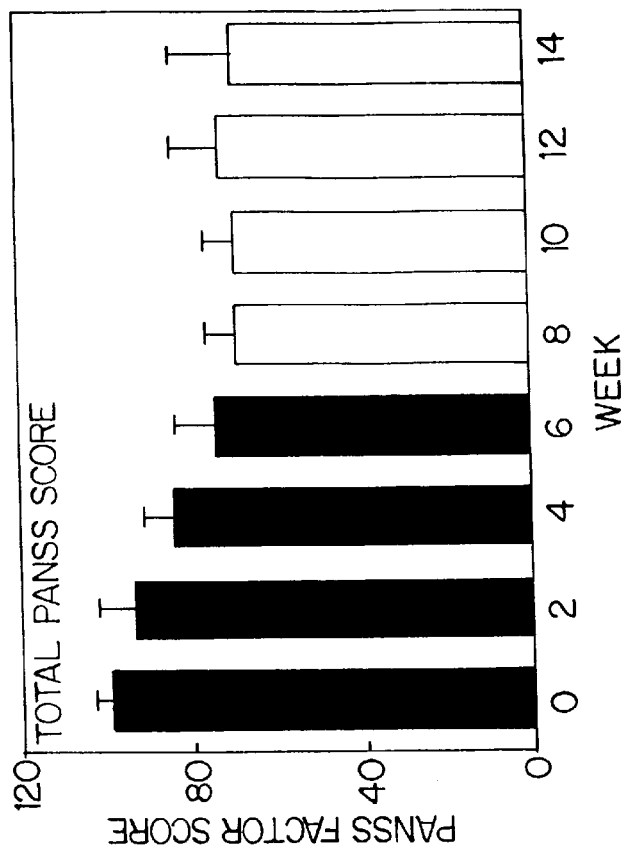
FIG. 3 (a)–(d) of the drawing depicts, from Study #2, three-factor and total PANSS scores during double-blind adjunctive treatment with glycine and during the subsequent placebo period in 7 subjects who received glycine during the first treatment arm.
Figure 3C:
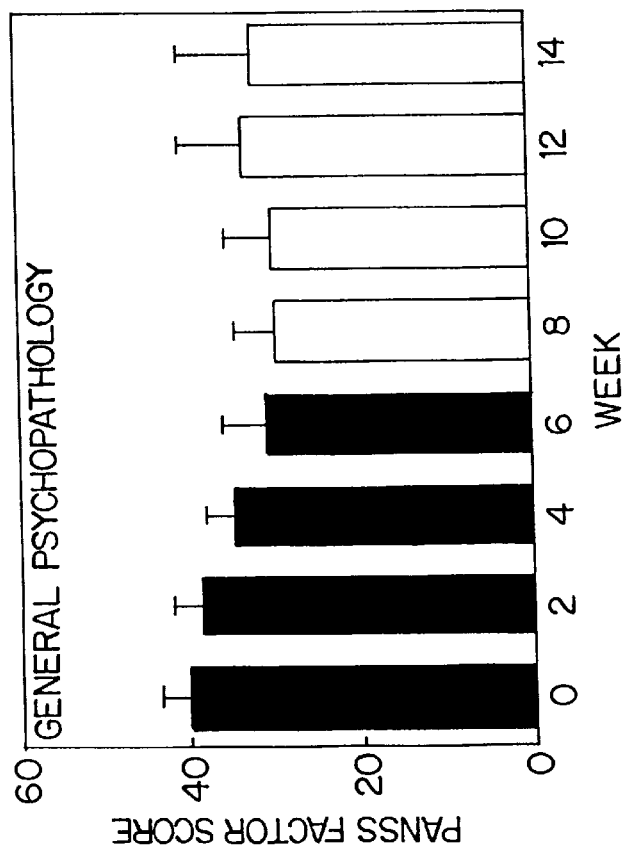

Because 7 of the 11 subjects received glycine during the initial double blind, it was possible to evaluate the degree to which symptom improvement was maintained throughout the subsequent placebo treatment period (FIG. 3). No change in positive symptoms occurred in these 7 subjects during any phase of the study, whereas negative symptoms improved significantly during the glycine treatment phase ($F(3,4)=45.7$, $p=0.001$) and remained stable thereafter, with no significant worsening occurring during the subsequent placebo phase ($F(3,4)=1.86$, $p=0.28$). Similarly general psychopathology improved significantly during the glycine treatment phase ($F(3,4)=19.2$, $p<0.01$) and remained stable thereafter ($F(3,4)=2.52$, $p=0.20$), indicating that the improvements observed during glycine treatment were maintained during the subsequent 8 weeks of the study period.

5-Factor Analysis of the PANSS

Figure 4C:
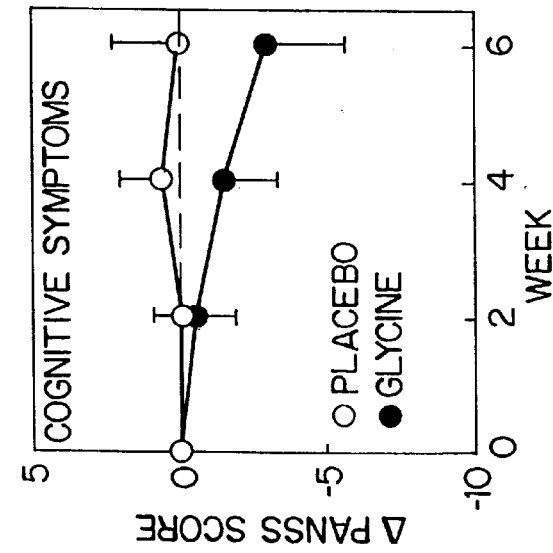
FIG. 4 (a)–(e) of the drawing depicts, from Study #2, five-factor PANSS change scores during double-blind adjunctive treatment with glycine and placebo (* $p<0.05$, * $p<0.01$, *** $p<0.001$).
Figure 4D:
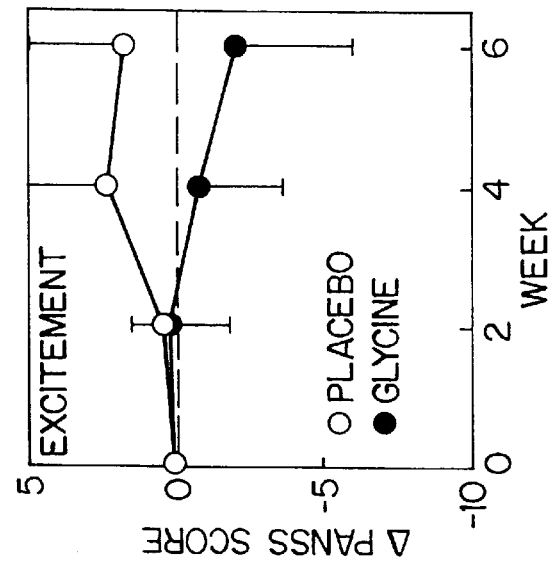
Figure 4E:
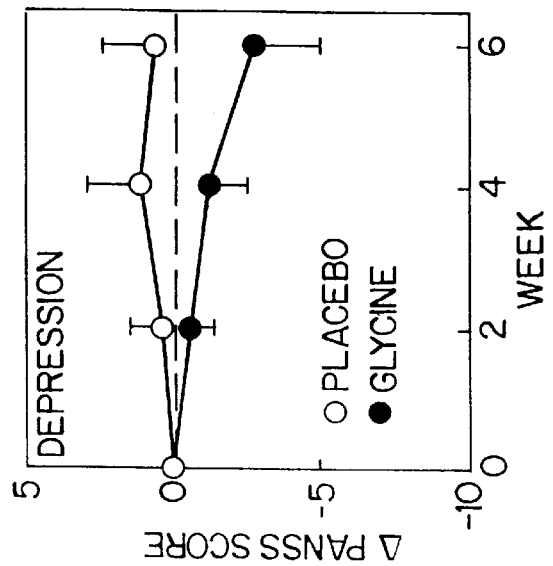

Although traditional analysis of the PANSS divides symptoms into positive, negative and general clusters, alternative analyses have been proposed that incorporate either 5 or 7 factors. The 5 factor model divides symptoms into clusters that are labeled positive, negative, cognitive, depression and excitement. In order to determine the degree to which glycine affected dimensions of schizophrenia other than positive and negative, a secondary analysis of the data was performed using the 5-factor components (FIG. 4). As in the 3-factor analysis, no significant reduction in PANSS positive symptoms were observed during either glycine or placebo treatment, while significant, progressive improvement was observed during the glycine-, but not placebo-, treatment period (treatment by time $F(3,8)=19.5$, $p<0.0001$). Using the 5-factor analysis, however, significant reductions were also observed for depression ($F(3,8)=7.23$, $p<0.02$) and cognitive symptoms ($F(3,8)=4.74$, $p<0.05$). Improvements in depression ($F(3,5)=2.13$, $p=0.22$) and cognitive impairment ($F(3,5)=0.89$, $p=0.51$) did not remain significant following covariation for changes in negative symptoms. In contrast, the effect of glycine on negative symptoms remained significant even following covariation for changes in cognitive impairment or depression ($F(3,5)=6.8$, $p=0.032$). The percentage reduction was greatest for negative symptoms ($41.0\pm15.4\%$ decrease vs. preglycine levels, $p<0.0001$), followed by depression ($23.0\pm17.9\%$, $p=0.002$) and cognitive impairment ($15.2\pm13.5\%$, $p=0.004$). Reductions in excitement ($11.9\pm26.3\%$, $p=0.17$) and positive symptoms ($9.4\pm20.5\%$, $p=0.16$) did not reach statistical significance.

TABLE 1

3 Mean (sd) PANSS factor scores during prestudy baseline

| Factor | Week −2 | Week 0 |
|---|---|---|
| Positive symptoms | 23.1 (3.6) | 23.6 (3.2) |
| Negative symptoms | 35.6 (3.2) | 37.0 (6.5) |
| General psychopathology | 44.9 (13.2) | 45.5 (13.4) |
| Total PANSS score | 103.6 (20.6) | 105.5 (18.9) |

TABLE 2

3-factor PANSS scores during double-blind treatment with glycine (60 g/day)

| PANSS | Treatment | PANSS Factor Scores — mean (sd) Treatment week | | | | Statistical (rmANOVA) Results Treatment | Time | Treat. X time |
|---|---|---|---|---|---|---|---|---|
| Positive | Glycine | 24.6 | 23.7 | 22.6 | 21.0 | F = 3.38 | F = 2.25 | F = 0.85 |
|  | Placebo | 20.6 | 20.2 | 21.5 | 20.9 |  |  |  |
| Negative | Glycine | 37.0 | 33.5 | 28.7 | 24.2 | F = 2.20 | F = 41.1 | F = 42.5 |
|  | Placebo | 27.8 | 27.1 | 27.4 | 26.9 |  |  |  |
| General | Glycine | 46.5 | 44.6 | 40.2 | 35.4 | F = 1.22 | F = 4.55 | F = 12.1 |
|  | Placebo | 38.1 | 38.6 | 41.8 | 40.5 |  |  |  |
| Total PANSS | Glycine | 108.1 | 101.8 | 91.7 | 80.6 | F = 2.93 | F = 16.6 | F = 13.4 |
|  | Placebo | 86.6 | 85.9 | 90.6 | 88.3 |  |  |  |

REFERENCES

1. Andreasen N (1989): The scale for the assessment of negative symptoms (SANS): conceptual and theoretical foundations. Br J Psychiatry 155 (suppl. 7):49–52
2. Costa J, Khaled E, Sramek J, Bunney W Jr, Potkin S G (1990): An open trial of glycine as an adjunct to neuroleptics in chronic treatment-refractory schizophrenics. J Clin Psychopharmacol 10:71–72.
3. D'Souza D C, Morrissey K, Abi-Saab D, Damon D, Gil R, Bennett A, Krystal J H (1995): Intravenous glycine and oral D-cycloserine effects on CSF amino acids, plasma hormones, and behavior in healthy humans: Implications for schizophrenia. Schiz Res 15:147, 1995.
4. Hariharan M, Naga S, VanNoord T (1993): Systematic approach to the development of plasma amino acid analyses by high-performance liquid chromatography with ultraviolet detection with precolumn derivatization using phenyl isothiocyanate. J Chromatogr 621:15–22.
5. Javitt D C and Zukin S R (1991): Recent advances in the phencyclidine model of schizophrenia. Am J Psychiatry 148: 1301–1308.
6. Javitt D C, Zylberman I, Zukin S R, Heresco-Levy U, Lindenmayer J P (1994): Amelioration of negative symptoms in schizophrenia by glycine. Am J Psychiatry 151:1234–1236.
7. Johnson J W. Ascher. P. Glycine potentiates the NMDA response in cultured mouse brain neurons. Nature. 325:529–31, 1987.
8. Kay S R, Fiszbein A, Opler L A (1987): The positive and negative syndrome scale (PANSS) for schizophrenia. Schiz Bull 13:261–276
9. Leiderman Eduardo, Zylberman Ilana, Zukin Stephen R., Cooper Thomas B, Javitt Daniel C. (1996): Preliminary Investigation of High-Dose Oral Glycine on Serum Levels and Negative Symptoms in Schizophrenia: An Open-Label Trial. Biol Psychiatry 39:213–215.
10. Potkin S G, Costa J, Roy S, Sramek J, Jin Y, Gulasekaram B (1992): Glycine in the treatment of schizophrenia—theory and preliminary results, in Novel Antipsychotic Drugs. Edited by Meltzer H Y. New York, Raven Press.
11. Rosse R B, Theut S K, Banay-Schwartz M, Leighton M, Scarcella E, Cohen C G, Deutsch S I (1989): Glycine adjuvant therapy to conventional neuroleptic treatment in schizophrenia: an open-label, pilot study. Clin Neuropharmacol 12:416–24.
12. Waziri R (1989): Glycine therapy of schizophrenia. Biol Psychiatry 1988, 23:210–211 [letter].
13. Potkin Steven G, Costa Jerome, Swati Roy, Sramek John, Jin Yi, Gulasekaram Bala (1992): Glycine in the Treatment of Schizophrenia Theory and Preliminary Results. Novel Antipsychotic Drugs, 179–188. New York, Raven Press.
14. Toth Eugene, Weiss Benjamine, Banay-Schwartz Miriam, Lajtha Abel (1986): Effect of Glycine Derivatives on Behavioral Changes induced by 3-Mercaptopropionic Acid or Phencyclidine in Mice. 11: 1–8.
15. Javitt, D. C. (1987): Negative Schizophrenia Symptomatology and the PCP Model of Schizophrenia, Hillside Journal of Clinical Psychiatry, 9, 12–35.

From the above, the positive effects of this invention on symptoms of schizophrenia can be seen.

The skilled artisan will be able to select other naturally occurring glycine precursors for use in providing a glycine-like antipsychotic effect.

Variations of the invention will be apparent to the skilled artisan.

What is claimed is:

1. A process for treating a human patient having a psychosis which comprises administering to said human D-serine.

* * * * *